United States Patent
Donnelly et al.

(10) Patent No.: US 8,834,538 B2
(45) Date of Patent: *Sep. 16, 2014

(54) METHOD OF PERFORMING ANTERIOR CRUCIATE LIGAMENT RECONSTRUCTION USING BIODEGRADABLE INTERFERENCE SCREW

(75) Inventors: Lisa M. Donnelly, Wayland, MA (US); Yufu Li, Bridgewater, NJ (US); Joan M. Sullivan, Hanover, MA (US); Gregory R. Whittaker, Stoneham, MA (US); J. Jenny Yuan, Neshanic Station, NJ (US)

(73) Assignee: DePuy Mitek, LLC, Raynham, MA (US)

( * ) Notice: Subject to any disclaimer, the term of this patent is extended or adjusted under 35 U.S.C. 154(b) by 376 days.

This patent is subject to a terminal disclaimer.

(21) Appl. No.: 13/191,078

(22) Filed: Jul. 26, 2011

(65) Prior Publication Data

US 2011/0282450 A1 Nov. 17, 2011

Related U.S. Application Data

(63) Continuation of application No. 10/673,737, filed on Sep. 29, 2003, now Pat. No. 8,016,865.

(51) Int. Cl.
*A61B 17/86* (2006.01)
*A61L 31/14* (2006.01)
*A61L 31/12* (2006.01)

(52) U.S. Cl.
CPC .............. *A61L 31/127* (2013.01); *A61L 31/148* (2013.01); *A61L 31/128* (2013.01)
USPC .......................................................... 606/301

(58) Field of Classification Search
USPC ........... 606/300, 301, 304, 321, 323, 331, 88, 606/104, 77; 623/13.12, 13.11, 13.14, 623/13.13, 13.18
See application file for complete search history.

(56) References Cited

U.S. PATENT DOCUMENTS

| | | | |
|---|---|---|---|
| 4,356,572 A | 11/1982 | Guillemin et al. |
| 4,643,734 A | 2/1987 | Lin |
| 4,645,503 A | 2/1987 | Lin et al. |
| 4,655,777 A | 4/1987 | Dunn et al. |
| 4,781,183 A | 11/1988 | Casey et al. |
| 4,950,270 A | 8/1990 | Bowman et al. |
| 5,108,755 A | 4/1992 | Daniels et al. |

(Continued)

FOREIGN PATENT DOCUMENTS

DE 2742128 A1 3/1978
EP 0615732 A1 9/1994

(Continued)

OTHER PUBLICATIONS

EP Search Report dated Feb. 15, 2005 for EP Appl. No. 04 25 5926.

(Continued)

*Primary Examiner* — Pedro Philogene
*Assistant Examiner* — David Comstock

(57) ABSTRACT

A method of replacing an ACL with a graft. The method provides for the drilling bone tunnels in a femur and a tibia. A replacement graft is provided having first and second ends. A biodegradable composite screw is provided. The screw is made from a biodegradable polymer and a bioceramic or a bioglass. At least one end of the graft is secured in a bone tunnel using the biodegradable composite screw.

11 Claims, 15 Drawing Sheets

(56) References Cited

U.S. PATENT DOCUMENTS

| | | |
|---|---|---|
| 5,116,337 A | 5/1992 | Johnson |
| 5,139,520 A | 8/1992 | Rosenberg |
| 5,275,601 A | 1/1994 | Gogolewski et al. |
| 5,364,400 A | 11/1994 | Rego, Jr. et al. |
| 5,478,355 A | 12/1995 | Muth et al. |
| 5,509,913 A | 4/1996 | Yeo |
| 5,552,454 A | 9/1996 | Kretschmann et al. |
| 5,584,836 A | 12/1996 | Ballintyn et al. |
| 5,603,716 A | 2/1997 | Morgan et al. |
| 5,618,314 A | 4/1997 | Harwin et al. |
| 5,626,612 A | 5/1997 | Bartlett |
| 5,632,748 A | 5/1997 | Beck, Jr. et al. |
| 5,679,723 A | 10/1997 | Cooper et al. |
| 5,681,873 A | 10/1997 | Norton et al. |
| 5,716,359 A | 2/1998 | Ojima et al. |
| 5,725,541 A | 3/1998 | Anspach, III et al. |
| 5,741,329 A | 4/1998 | Agrawal et al. |
| 5,747,390 A | 5/1998 | Cooper et al. |
| 5,766,618 A | 6/1998 | Laurencin et al. |
| 5,849,013 A | 12/1998 | Whittaker et al. |
| 5,868,749 A | 2/1999 | Reed |
| 5,871,504 A | 2/1999 | Eaton et al. |
| 5,879,372 A | 3/1999 | Bartlett |
| 5,955,529 A | 9/1999 | Imai et al. |
| 5,962,007 A | 10/1999 | Cooper et al. |
| 5,968,047 A | 10/1999 | Reed |
| 5,971,987 A | 10/1999 | Huxel et al. |
| 5,977,204 A | 11/1999 | Boyan et al. |
| 5,980,252 A | 11/1999 | Samchukov et al. |
| 5,980,574 A | 11/1999 | Takei et al. |
| 6,001,100 A | 12/1999 | Sherman et al. |
| 6,165,203 A | 12/2000 | Krebs |
| 6,165,486 A | 12/2000 | Marra et al. |
| 6,214,007 B1 | 4/2001 | Anderson |
| 6,254,562 B1 | 7/2001 | Fouere |
| 6,283,973 B1 | 9/2001 | Hubbard et al. |
| 6,325,804 B1 | 12/2001 | Wenstrom, Jr. et al. |
| 6,331,313 B1 | 12/2001 | Wong et al. |
| 6,402,766 B2 | 6/2002 | Bowman et al. |
| 6,406,498 B1 | 6/2002 | Tormala et al. |
| 6,471,707 B1 | 10/2002 | Miller et al. |
| 6,562,071 B2 | 5/2003 | Jarvinen |
| 6,565,573 B1 | 5/2003 | Ferrante et al. |
| 6,749,620 B2 | 6/2004 | Bartlett |
| 6,773,436 B2 | 8/2004 | Donnelly et al. |
| 6,866,666 B1 | 3/2005 | Sinnott et al. |
| 6,916,321 B2 | 7/2005 | TenHuisen et al. |
| 7,012,106 B2 | 3/2006 | Yuan et al. |
| 8,016,865 B2 | 9/2011 | Donnelly et al. |
| 2001/0007074 A1 | 7/2001 | Strobel et al. |
| 2001/0041937 A1 | 11/2001 | Rieser et al. |
| 2002/0072797 A1 | 6/2002 | Hays et al. |
| 2002/0099411 A1 | 7/2002 | Bartlett |
| 2002/0147463 A1 | 10/2002 | Martinek |
| 2002/0161371 A1 | 10/2002 | Bezemer et al. |
| 2003/0006533 A1 | 1/2003 | Shikinami et al. |
| 2003/0009235 A1 | 1/2003 | Manrique et al. |
| 2003/0026675 A1 | 2/2003 | McGovern et al. |
| 2003/0040695 A1 | 2/2003 | Zhao et al. |
| 2003/0065331 A1 | 4/2003 | Donnelly et al. |
| 2003/0074002 A1 | 4/2003 | West |
| 2003/0074004 A1 | 4/2003 | Reed |
| 2003/0105471 A1 | 6/2003 | Schlapfer et al. |
| 2003/0125744 A1 | 7/2003 | Contiliano et al. |
| 2003/0125749 A1 | 7/2003 | Yuan et al. |
| 2003/0233095 A1 | 12/2003 | Urbanski et al. |
| 2004/0001890 A1 | 1/2004 | Rosenblatt et al. |
| 2004/0006346 A1 | 1/2004 | Holmen et al. |
| 2004/0153075 A1 | 8/2004 | Roger |
| 2004/0181257 A1 | 9/2004 | Bartlett |
| 2004/0193285 A1 | 9/2004 | Roller et al. |
| 2004/0243178 A1 | 12/2004 | Haut et al. |
| 2004/0243180 A1 | 12/2004 | Donnelly et al. |
| 2005/0216016 A1 | 9/2005 | Contiliano et al. |
| 2005/0222618 A1 | 10/2005 | Dreyfuss et al. |
| 2005/0222619 A1 | 10/2005 | Dreyfuss et al. |
| 2005/0267479 A1 | 12/2005 | Morgan et al. |
| 2006/0015108 A1 | 1/2006 | Bonutti |
| 2006/0020266 A1 | 1/2006 | Cooper |
| 2006/0122624 A1 | 6/2006 | Truckai et al. |
| 2006/0149266 A1 | 7/2006 | Cordasco |
| 2006/0178748 A1 | 8/2006 | Dinger et al. |
| 2006/0229671 A1 | 10/2006 | Steiner et al. |
| 2006/0264531 A1 | 11/2006 | Zhao |
| 2007/0093895 A1 | 4/2007 | Donnelly et al. |

FOREIGN PATENT DOCUMENTS

| | | |
|---|---|---|
| EP | 0714666 A1 | 6/1996 |
| JP | 2002-035018 A | 2/2002 |
| JP | 2003-506158 T | 2/2003 |
| JP | 2003-180816 A | 7/2003 |
| WO | WO-9001342 A1 | 2/1990 |
| WO | WO-9600592 | 1/1996 |
| WO | WO-0001426 A1 | 1/2000 |
| WO | WO-2003/011343 A1 | 2/2003 |

OTHER PUBLICATIONS

Fink et al., "Bioabsorbable Polyglyconate Interference Screw Fixation in Anterior Cruciate Ligament Reconstruction: A Prospective Computed Tomology-Controlled Study," Arthroscopy: The Journal of Arthroscopic and Related Surgery, vol. 16, No. 5 Jul.-Aug.), 2000: pp. 491-498.

J.L. Leray, "Biodegradable Composite Materials for Bone Surgery," Trans. Soc. Biomater., 1, 70 (1977).

Office Action dated Aug. 16, 2005 in U.S. Appl. No. 10/673,737.
Office Action dated Dec. 31, 2007 in U.S. Appl. No. 10/673,737.
Office Action dated Feb. 19, 2010 in U.S. Appl. No. 10/673,737.
Office Action dated Feb. 23, 2006 in U.S. Appl. No. 10/673,737.
Office Action dated Jan. 26, 2005 in U.S. Appl. No. 10/673,737.
Office Action dated Jun. 1, 2007 in U.S. Appl. No. 10/673,737.
Office Action dated May 28, 2009 in U.S. Appl. No. 10/673,737.
Office Action dated Sep. 18, 2008 in U.S. App. No. 11/604,427.

Weiler et al, "Biodegradable Implants in Sports Medicine: The Biological Base," Arthroscopy: The Journal of Arthroscopic and Related Surgery, vol. 16, No. 3 (Apr. 2000): pp. 305-321.

Smith et al., "Fracture of Bilok Interference Screws on Insertion During Anterior Cruciate Ligament Reconstruction," Arthroscopy: The Journal of Arthroscopic and Related Surgery, vol. 19, No. 9 (Nov. 2003): e115-e117.

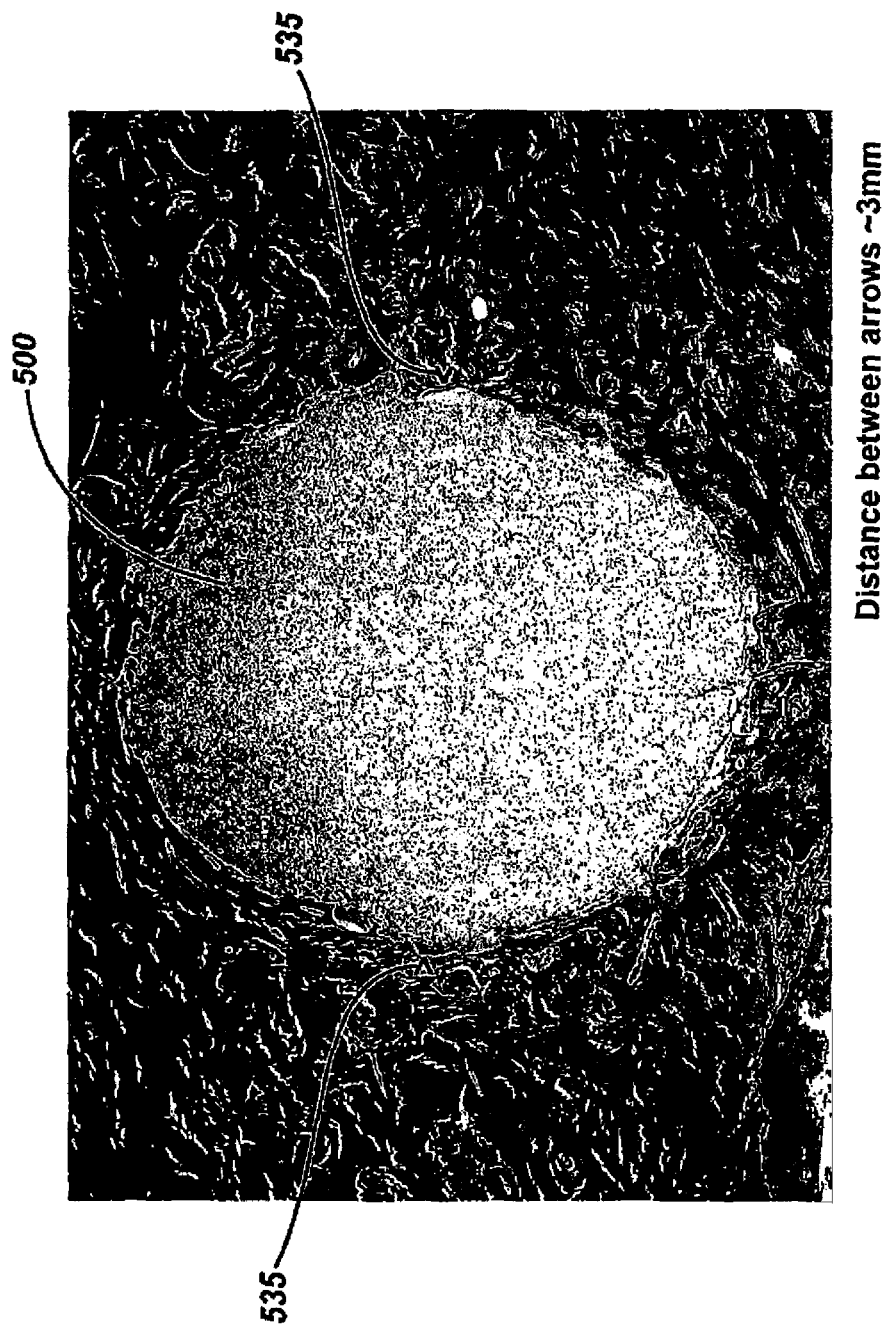

METHOD OF PERFORMING ANTERIOR CRUCIATE LIGAMENT RECONSTRUCTION USING BIODEGRADABLE INTERFERENCE SCREW

CROSS REFERENCE TO RELATED APPLICATIONS

The present application is a continuation of U.S. patent application Ser. No. 10/673,737 filed on Sep. 29, 2003 now U.S. Pat. No. 8,016,865 and entitled "Method Of Performing Anterior Cruciate Ligament Reconstruction Using Biodegradable Interference Screw," which is hereby incorporated by reference in its entirety.

FIELD

The field of art to which this invention relates is surgical procedures for the repair of an anterior cruciate ligament, more specifically, a surgical procedure for affixing an anterior cruciate ligament graft into a bone using a biodegradable interference screw.

BACKGROUND

The knee joint is one of the strongest joints in the body because of the powerful ligaments that bind the femur and tibia together. Although the structure of the knee provides one of the strongest joints of the body, the knee may be one of the most frequently injured joints, e.g., athletes frequently stress and tear knee ligaments. The large number of ligament injuries has given rise to considerable innovative surgical procedures and devices for replacing and reconstructing torn or dislocated ligaments, typically involving grafting autografts, allografts, or a synthetic construct, to the site of a torn or dislocated ligament. For example, the replacement of an anterior cruciate ligament (ACL) may involve transplanting a portion of the patellar tendon, looped together portions of semitendinosus-gracilis (hamstring) tendons, or donor Achilles tendons, to attachment sites in the region of the knee joint.

Tears or ruptures of an anterior cruciate ligament of a knee (ACL) typically require a major surgical intervention wherein a replacement graft is mounted to the ends of the bones surrounding the knee in order to reconstruct the knee. A ruptured or damaged ACL typically results in serious symptoms such as knee instability resulting in diminished ability to perform high level or recreational sports, or in some cases daily activities relating to motility. Although the use of knee braces may alleviate some of these symptoms, the potential long term effects of a damaged ACL include meniscal damage and articular cartilage damage.

The basic steps in a conventional ACL reconstruction procedure include: harvesting a graft made from a portion of the patellar tendon with attached bone blocks; preparing the graft attachment site (e.g., drilling holes in opposing bones of the joint in which the graft will be placed); placing the graft in the graft attachment site; and rigidly fixing the bone blocks in place within the graft site, i.e., the holes or "bone tunnels". The screws used to fix the graft in place are called "interference screws" because they are wedged between the bone block and the wall of the bone tunnel into which the bone block fits. Typically, there is very little space between the bone block and the inner wall of the bone tunnel in the bone at the fixation site.

Several types of surgical procedures have been developed to replace the ACL. Although repair would be a preferred procedure, it is not typically possible since the end of the torn ACL is typically not of sufficient length to reattach successfully. However, reconstructions can be made to a damaged ACL.

There are several types of conventional replacement grafts that may be used in these replacement procedures. In all procedures tibial and femoral tunnels are drilled by the surgeon using conventional techniques. Known, conventional drill guides and drills are used. In one type of procedure known as a bone-tendon-bone procedure, an autograft tendon is harvested from the patellar tendon along with an attached bone block on one end harvested from the patella and a harvested bone block on the other end harvested from the tibia. In order to secure the graft in the knee, one end is mounted into the tibial tunnel and other end is mounted into the femoral tunnel. This is done by mounting the opposed bone blocks in the tibial and femoral tunnels, respectively, in the following manner. A guide pin is passed through the tibial tunnel, into the fermoral tunnel and out through the lateral femoral cortex. Suture is used to attach the graft to the proximal end of the guide pin. The distal end of the guide pin is then pulled out of the lateral cortex of the femur and the graft is pulled into the knee (femoral and tibial tunnels). Once the bone blocks are emplaced in the respective tibial and femoral tunnels, the blocks are secured in place in the following manner. One method of securing or fixing the ends of the graft in the tunnels is to use a conventional metallic interference screw. The screw is inserted into the opening of a tunnel and placed in between the graft and the interior surface of the bone tunnel. It is then turned and screwed into the tunnels, thereby forcing the end of the graft against an interior surface of the bone tunnel. The ends of graft are secured and maintained in place in the tunnel by means of a force fit provided by the interference screw.

Another surgical procedure for the replacement of an anterior cruciate ligament involves providing a graft ligament without attached bone blocks. The graft can be an autograft or an allograft. The autografts that are used may typically be harvested from the hamstring tendons or the quadriceps tendons. The allografts that are conventionally used are harvested from cadaveric sources, and may include the hamstring tendons, quadriceps tendons Achilles tendon, and tibialus tendons. If desired, and if readily available, it may possible to use synthetic grafts or xenografts. Tibial and femoral tunnels are similarly drilled in the tibia and femur respectively using conventional techniques, drill guides and drills. Once the tunnels have been drilled, the surgeon then pulls the graft through the tibial and femoral tunnels using conventional techniques such that one end of the graft resides in the tibial tunnel and the other end of the graft resides in the femoral tunnel. For example, one conventional technique for pulling a graft through the tunnels is to attach the graft to the proximal end of a guide pin using conventional surgical suture. The guide pin is then passed through the tibial tunnel, into the femoral tunnel, and out though the femoral cortex. The distal end of the guide pin is then pulled out of the lateral cortex of the femur and the graft is pulled into the knee (femoral and tibial tunnels). After the surgeon has emplaced and positioned the ends of the graft in the respective tunnels, the graft ends need to be secured and fixed in place to complete the replacement procedure. One method of securing or fixing the ends of the graft in the tunnels is to use a conventional metallic interference screw. The screw is inserted into the opening of a tunnel and placed in between the graft and the interior surface of the bone tunnel. It is then turned and screwed into the tunnels, thereby forcing the end of the graft against an interior surface of the bone tunnel. The ends of the graft are secured and maintained in place in the tunnel by means of a force fit provided by the bone screw.

Interference screws for anchoring ligaments to bone are typically fabricated from medically approved metallic materials that are not naturally degraded by the body. One potential disadvantage of such screws is that once healing is complete, the screw remains in the bone. An additional disadvantage of a metal screw is that in the event of a subsequent rupture or tear of the graft, it may be necessary to remove the metal screw from the bone site. Metallic screws may include a threaded shank joined to an enlarged head having a transverse slot or hexagonal socket formed therein to engage, respectively, a similarly configured, single blade or hexagonal rotatable driver for turning the screw into the bone. The enlarged heads on such screws can protrude from the bone tunnel and can cause chronic irritation and inflammation of surrounding body tissue.

Permanent metallic medical screws in movable joints can, in certain instances, cause abrading of ligaments during normal motion of the joint. Screws occasionally back out after insertion, protruding into surrounding tissue and causing discomfort. Furthermore, permanent metallic screws and fixation devices may shield the bone from beneficial stresses after healing. It has been shown that moderate periodic stress on bone tissue, such as the stress produced by exercise, helps to prevent decalcification of the bone. Under some conditions, the stress shielding which results from the long term use of metal bone fixation devices can lead to osteoporosis.

Biodegradable interference screws have been proposed to avoid the necessity of surgical removal after healing. Because the degradation of a biodegradable screw occurs over a period of time, support load is transferred gradually to the bone as it heals. This reduces potential stress shielding effects.

In order to overcome the disadvantages that may be associated with metal interference screws, interference screws made from biodegradable polymers are known in this art. For example, it is known to use an interference screw made from polylactic acid. Ideally, the biodegradable interference screw will rapidly absorb or break down and be replaced by bone. However, it is known that screws made from polylactic acid tend to maintain their structural integrity for very long periods of time thereby preventing the desired bone in growth. Attempts have been made to improve the bone regeneration process by using other biodegradable polymers and copolymers of lactic acid that resorb or absorb more quickly. The problem often associated with these quicker absorbing polymers or copolymers is that the bone regeneration may proceed at a much slower rate than the rate of resorption, resulting in premature mechanical failure of the screw and a resulting pull out of the graft end from the femoral tunnel. Some of the absorbable interference screws of the prior art may take several years to absorb, and may result in a fibrous tissue mass or cyst being left behind, not bone. This lack of bone in-growth may create fixation problems if the ACL is torn again, necessitating a new graft replacement. In addition, if the screw absorbs too slowly, the screw will need to be removed in the event of a subsequent failure of the graft.

Accordingly, what is needed in this art is a novel method of performing an ACL replacement graft procedure using a novel interference screw made from a biodegradable material which rapidly absorbs or degrades and promotes bone in-growth.

SUMMARY

Therefore, it is an object of the present invention to provide a novel method of replacing a ruptured or injured anterior cruciate ligament with a graft using a novel biodegradable interference screw consisting of a composite of a biodegradable polymer and a biodegradable ceramic or bioglass.

Accordingly, a novel method of repairing an anterior cruciate ligament in the knee is disclosed. A replacement graft is provided having a first end and a second end. A bone tunnel is drilled in the tibia. A bone tunnel is also drilled in the tibia. The first end of the graft is mounted in the femoral bone tunnel. The second end of the graft is mounted in the tibial bone tunnel. A biodegradable, composite interference screw is provided. The interference screw is made from a copolymer of poly (lactic acid) and poly(glycolic acid) and a bioceramic. The biodegradable screw is inserted into the femoral bone tunnel between an interior surface of the femoral bone tunnel and the first end of the graft. The interference screw is rotated such that the screw is substantially contained within the femoral bone tunnel, and the first end of the graft is fixed in place between the interference screw and a section of the interior surface of the femoral bone tunnel.

These and other features, aspects and advantages of the present invention will become more apparent from the following description and accompanying drawings.

BRIEF DESCRIPTION OF THE DRAWINGS

The invention will be more fully understood from the following detailed description taken in conjunction with the accompanying drawings, in which:

FIG. 11D is a histological section of a PLA bone pin containing [beta]-tricalcium phosphate and surrounding tissue.

DETAILED DESCRIPTION

Figure 1A:
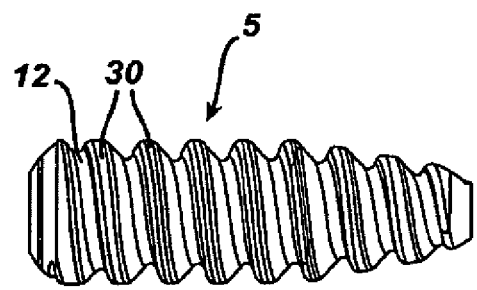
FIG. 1A is a side view of a biodegradable interference bone screw useful in the method of the present invention.

The novel interference screws of the present invention are a composite of a biodegradable polymer or copolymer and a bioceramic. The term biodegradable as used herein is defined to mean materials that degrade in the body and then are either absorbed into or excreted from the body. The term bioceramic as defined herein is defined to mean ceramic and glass materials that are compatible with body tissue. The bioceramics are preferably biodegradable.

The biodegradable polymers that can be used to manufacture the composite screws used in the novel process of the present invention include biodegradable polymers selected from the group consisting of aliphatic polyesters, polyorthoesters, polyanhydrides, polycarbonates, polyurethanes, polyamides and polyalkylene oxides. Preferably, the biodegradable polymers are aliphatic polyester polymers and copolymers, and blends thereof. The aliphatic polyesters are typically synthesized in a ring opening polymerization. Suitable monomers include but are not limited to lactic acid, lactide (including L-, D-, meso and D, L mixtures), glycolic acid, glycolide, .epsilon.-caprolactone, p-dioxanone (1,4-dioxan-2-one), trimethylene carbonate (1,3-dioxan-2-one), .delta.-valerolactone, and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80.degree. C. to about 240.degree. C., preferably from about 100.degree. C. to about 220.degree. C., until the desired molecular weight and viscosity are achieved. It is particularly preferred to use a copolymer of poly(lactic acid) and poly(glycolic acid). In particular, a copolymer of about 85 mole percent poly(lactic acid) and about 15 mole percent poly(glycolic acid).

The bioceramics that can be used in the composite screws used in the novel process of the present invention include ceramics comprising mono-, di-, tri-, [alpha]-tri-, [beta]-tri-, and tetra-calcium phosphate, hydroxyapatite, calcium sulfates, calcium oxides, calcium carbonates, magnesium calcium phosphates. It is particularly preferred to use a [beta]-tritricalcium phosphate.

In addition to bioceramics, bioglasses may also be used in the composite screws. The bioglasses may include phosphate glasses and bioglasses.

The amount of the bioceramic or bioglass in the composite interference screw will be sufficient to effectively promote bone in-growth. Typically the amount will be about 2.0 Vol. % to about 25.0 Vol. %, and preferably about 15.0 Vol. %.

The composite, biodegradable interference screws useful in the present invention are manufactured in conventional extrusion and molding processes using conventional extruding and molding equipment. In a typical process, dry biodegradable polymer pellets and dry bioceramic or bioglass are metered into a conventional heated screw extruder. The materials are heated and blended in the extruder for a sufficiently effective residence time to provide a viscous composite having a uniform distribution of the particles of bioglass or bioceramic. Then the viscous composite is cooled and chopped to form pellets of the homogenous composite. The interference screws may be molded in a conventional injection molder. In a typical injection molder, pellets of composite are fed into a barrel, passed through a heating zone to melt the polymer, then pushed forward through a nozzle and into the cavity of a chilled mold. After cooling, the mold is opened, and the part is ejected.

Figure 1B:
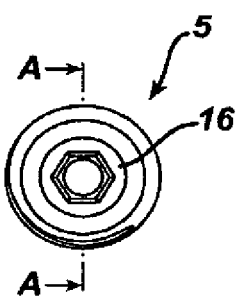
FIG. 1B is an end view of the interference bone screw of FIG. 1A.
Figure 1C:
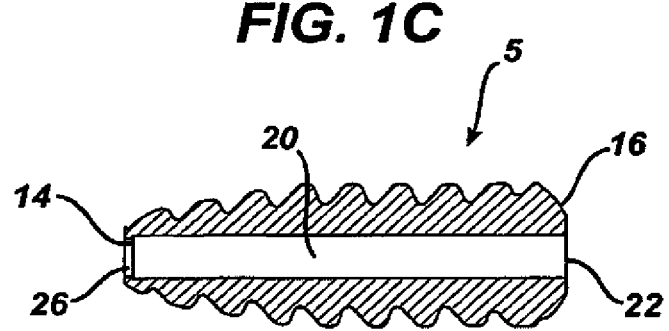
FIG. 1C is a cross-sectional view of the inference bone screw of FIG. 1B taken along view line A-A.
Figure 2:
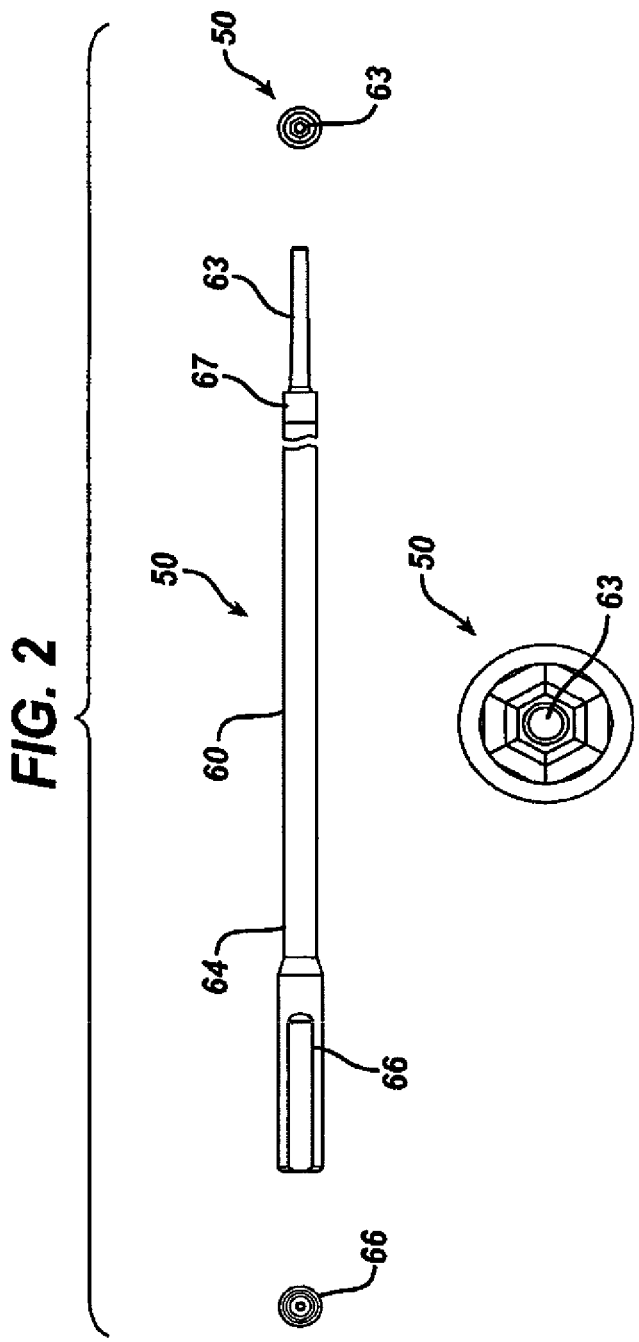
FIG. 2 is a side view of a driver device useful for emplacing the bone screw of FIG. 1 in a bone tunnel.

A biodegradable interference screw 5 of the present invention is seen in FIGS. 1A-C. The screw 5 is seen to have an elongate body 10 having a cannulated passage 20 therethrough, with proximal socket opening 22 and distal opening 26. The body 10 is seen to have a plurality of thread flights 30 extending from the outer surface 12. The body 10 is seen to have distal end 14 and proximal end 16. A driver 50 for inserting or emplacing the crew 5 in a bone tunnel is seen in FIG. 2. The driver 50 has an elongated rod member 60 having distal end 62 and proximal end 64. Distal end 62 is seen to have a driver 63 extending therefrom having a hexagonal configuration for mating with socket 22. The screw 5 is mounted to driver 50 by inserting the driver 63 of distal end 62 into the mating proximal socket end 22 of the passage 20.

The biodegradable composite interference screws described herein are used in the novel ACL reconstruction procedure of the present invention in the following manner as illustrated if FIGS. 3-10. Prior to reconstructing the ACL using a bone-tendon-bone graft, a patient is prepared for surgery in a conventional manner. The patient's knee 100 is prepared for surgery in a conventional manner including swabbing the skin around the knee with a conventional antiseptic solution, and draping the knee. The knee 100 is then angulated by the surgeon in a conventional manner to facilitate the surgical procedure. The patient is then anesthetized in a conventional manner using conventional anesthetics, either general or local at the discretion of the surgeon. As seen in FIG. 1, the knee 100 is seen to have a femur 150 having a distal end 160 and a tibia 130 having a proximal end 140. Proximal end 140 is seen to have a tibial plateau 141. Extending from the distal end 160 of femur 150 are the femoral condyles 170 separated by notch 175. For the sake of illustration, the tendons, cartilage, fascia, soft tissue and skin are not shown. The knee 100 is accessed by the surgeon using a conventional arthroscope that is inserted though a conventional cannula, that has been previously emplaced in the knee 100 in a conventional manner through an incision in the skin covering the knee 100. A flow of sterile saline is initiated through channels in the arthroscope into the knee 100. The stumps of the ACL are removed from the surfaces of the tibial plateau 141 and the chondryl notch 175 using conventional shavers that are inserted through the cannula. A bone-tendon-bone graft 200 is harvested and prepared by the surgeon in a conventional manner. The graft 200 is harvested by making an incision in the skin over the knee 100 down the anterior patella to the tibial. A conventional sagittal saw is then used to harvest the opposed bone plugs 220 that are connected by harvested patellar tendon segment 210. The tendon segment 210 is cut from the patellar tendon in a conventional manner using a scalpel. If desired, a graft without bone blocks attached may also be used in the method of the present invention.

The procedure continues by mounting a conventional tibial drill guide (not shown) to the proximal end of the tibia 130. A conventional guide pin 250 is inserted into the drill guide and mounted to a conventional surgical drill. The guide pin 250 is seen to have elongated body 252 having distal cutting end 254 and proximal end 255 with suture mounting opening 257. The guide pin 250 is drilled into the front of the tibia 130 in a conventional manner until the distal end 254 exits out from the tibial plateau 141. The drill guide is then removed from the tibia 130 and a conventional surgical reamer is placed over the guide pin 250 and turned to ream out a tibial tunnel 280 having a passage 282, an inner tunnel wall 283, a top opening 284 out of the tibial plateau 141 and a bottom opening 286 out through the tibia 130. Then the reamer and the guide pin 250 are removed from the tibial tunnel 280 and a conventional femoral aimer device (not shown) is inserted into tibial tunnel 280 and manipulated until the distal end of the femoral aimer engages the appropriate location on the femoral notch 175. Then the guide pin 250 is inserted through a passage in the femoral aimer, and the guide pin 250 is mounted to a conventional surgical drill and drilled into the femoral notch such that the distal end exits out through the lateral side of the femur 150 and through the skin overlying that section of the femur 150. Next, the femoral aimer is removed from the knee 100 and a conventional surgical bone reamer is placed over the guide pin 250 and moved through the tibial tunnel 280, and a femoral tunnel 290 is drilled though the femur having a passage 292, an inner tunnel wall 293, an upper opening 294 out through the lateral side of the femur 130 and a bottom opening 296 out of the femoral notch 175. The reamer is then removed from the bone tunnel 290.

Figure 3:
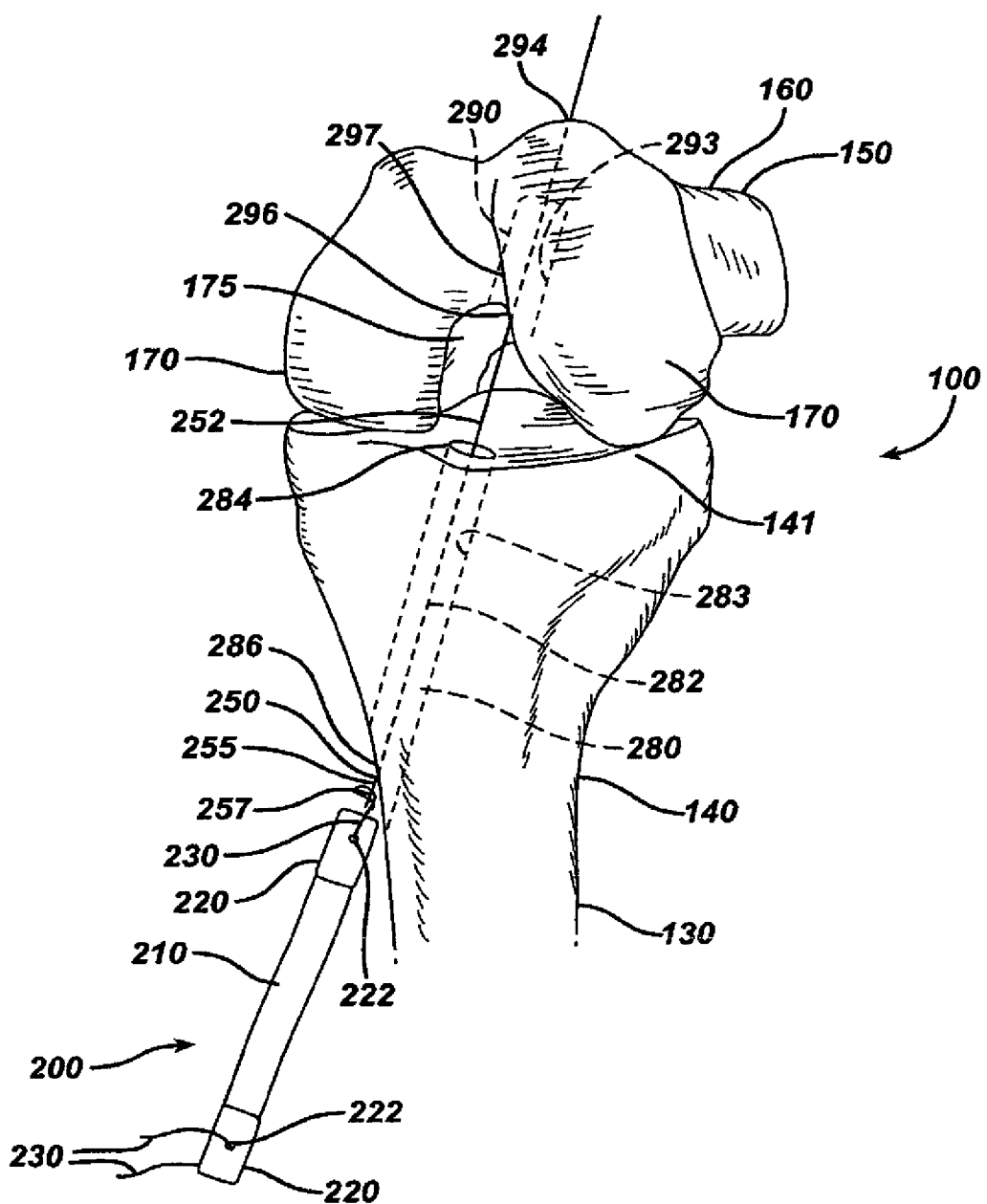
FIG. 3 illustrates a bone-tendon-bone graft prior to emplacement in a knee for an ACL reconstruction.
Figure 4:
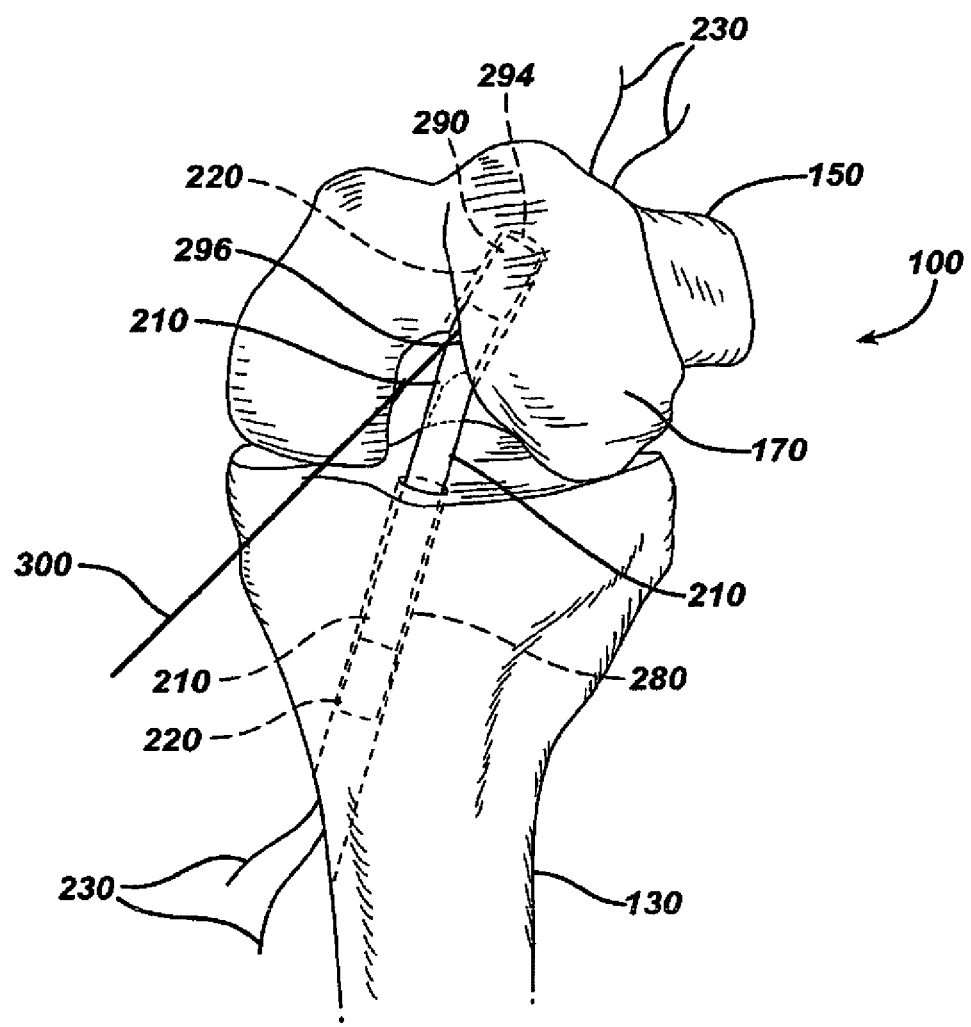
FIG. 4 shows a guide wire placed into the femoral tunnel between the tunnel wall and the bone block.
Figure 5:
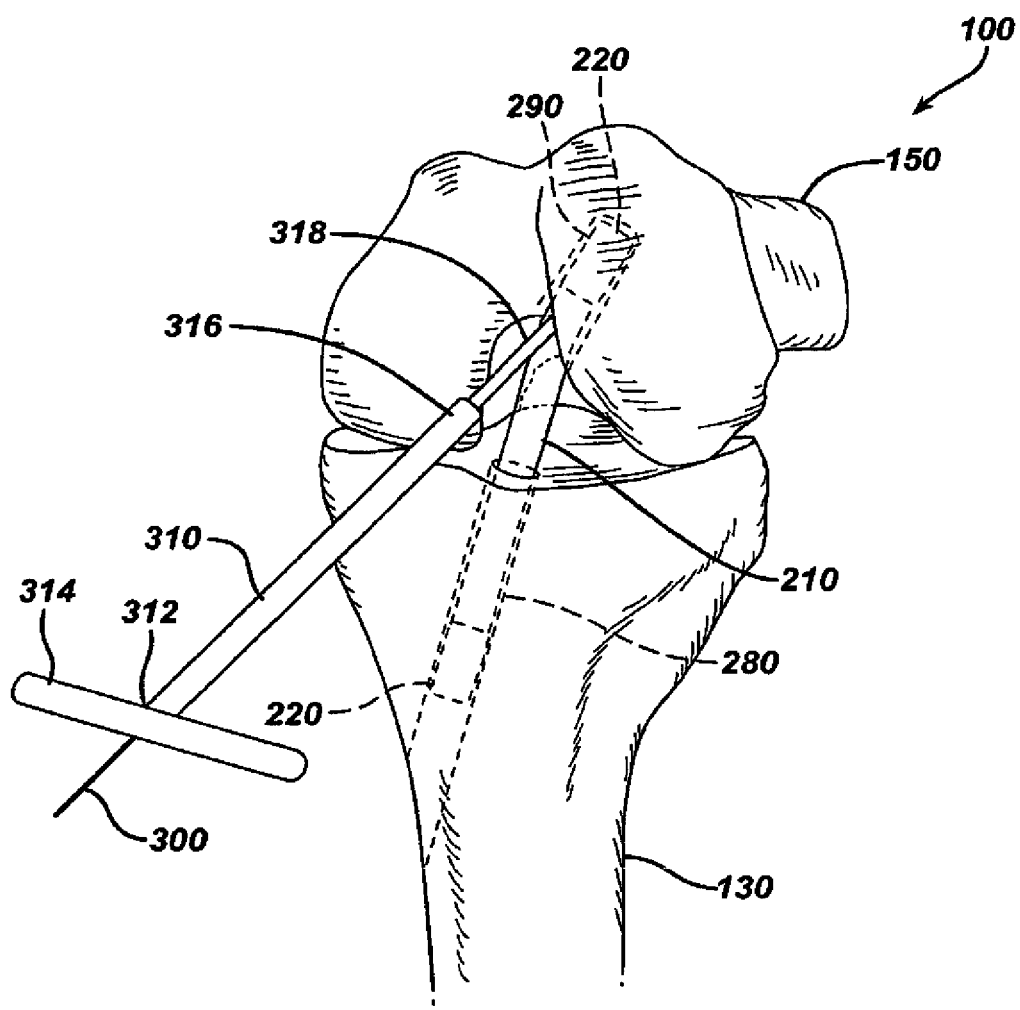
FIG. 5 illustrates a conventional tap being used to tap a hole between the wall and the bone block.
Figure 6:
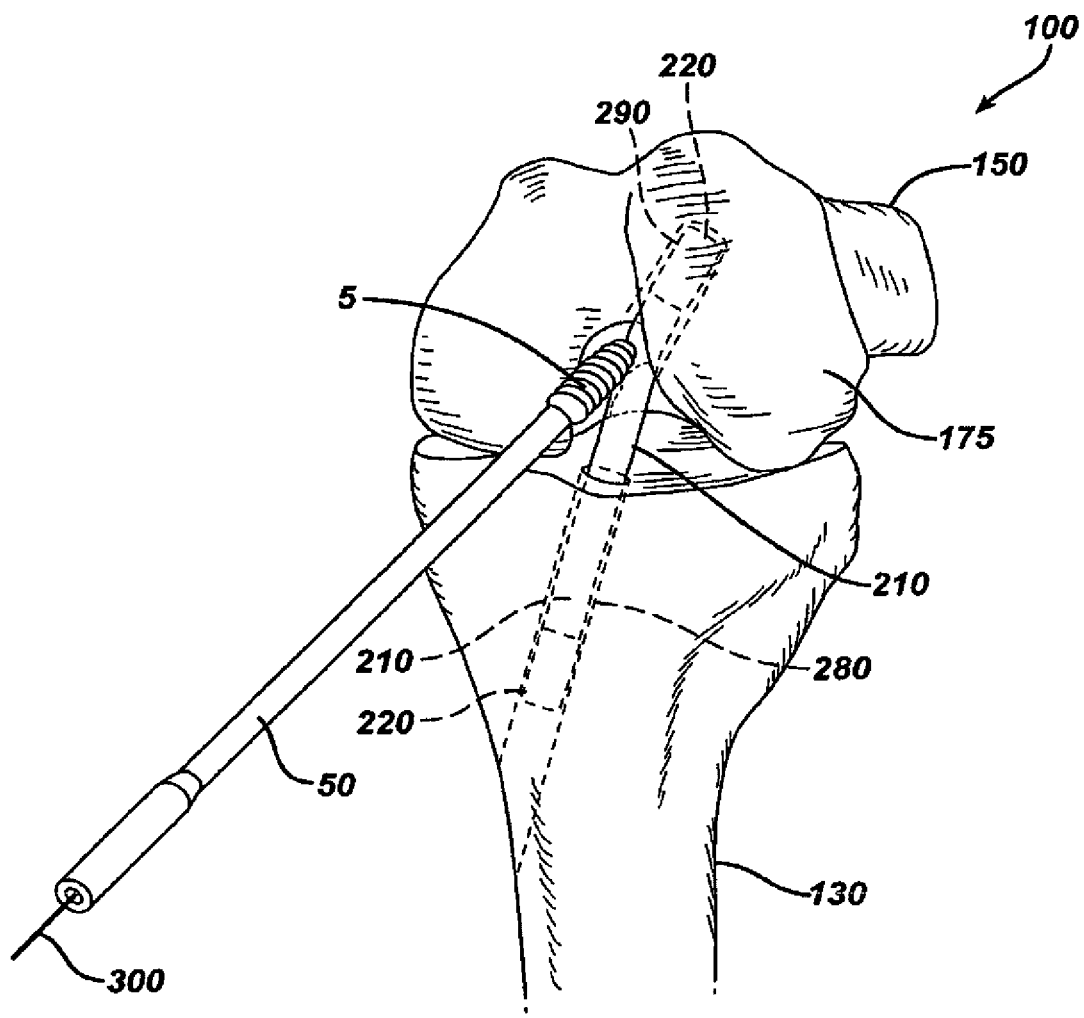
FIG. 6 shows a biodegradable interference screw being inserted into the femoral tunnel between the tunnel wall and the bone block.
Figure 7:
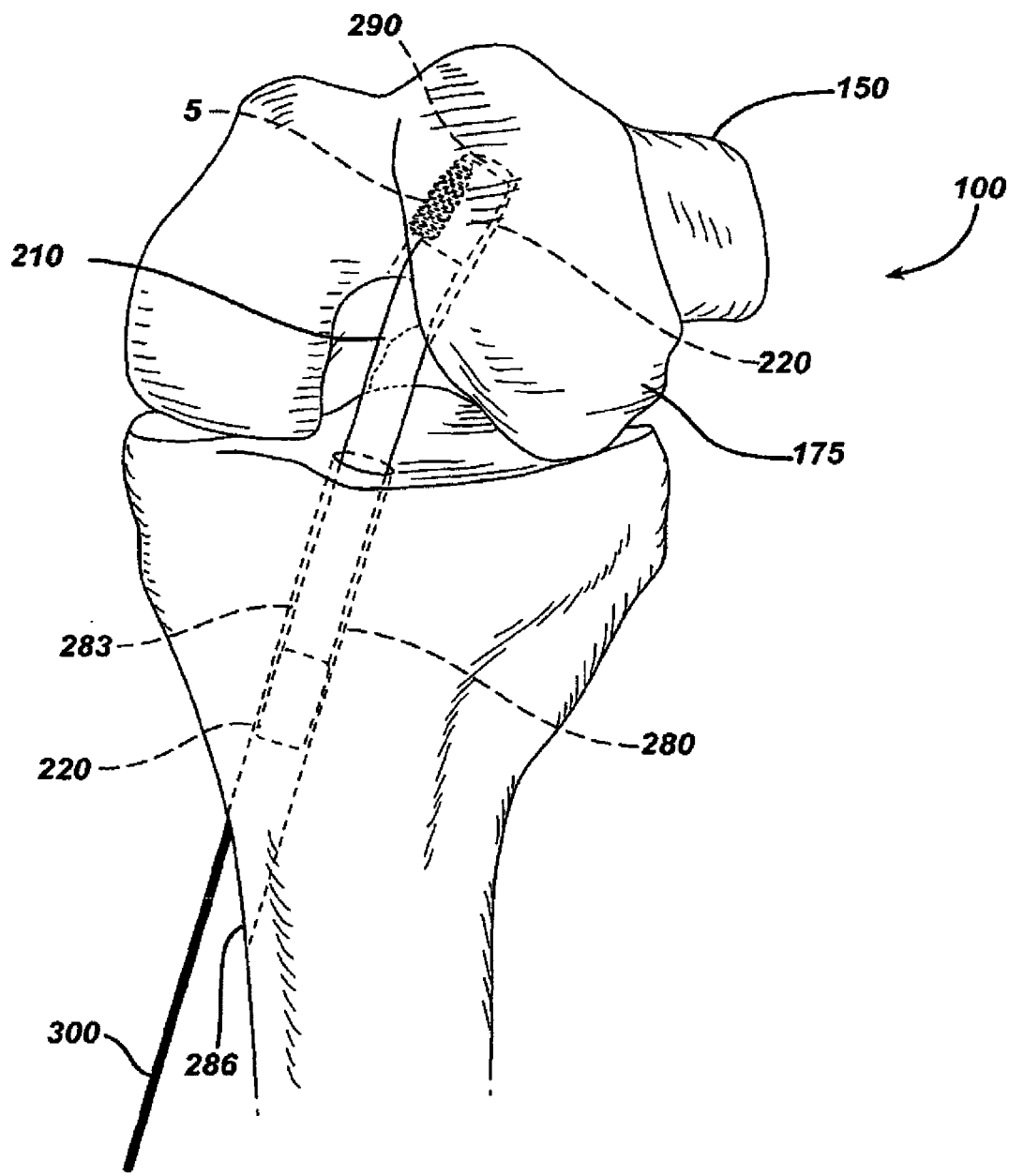
FIG. 7 illustrates a guide wire placed into the tibial tunnel between the tunnel wall and the bone block.
Figure 8:
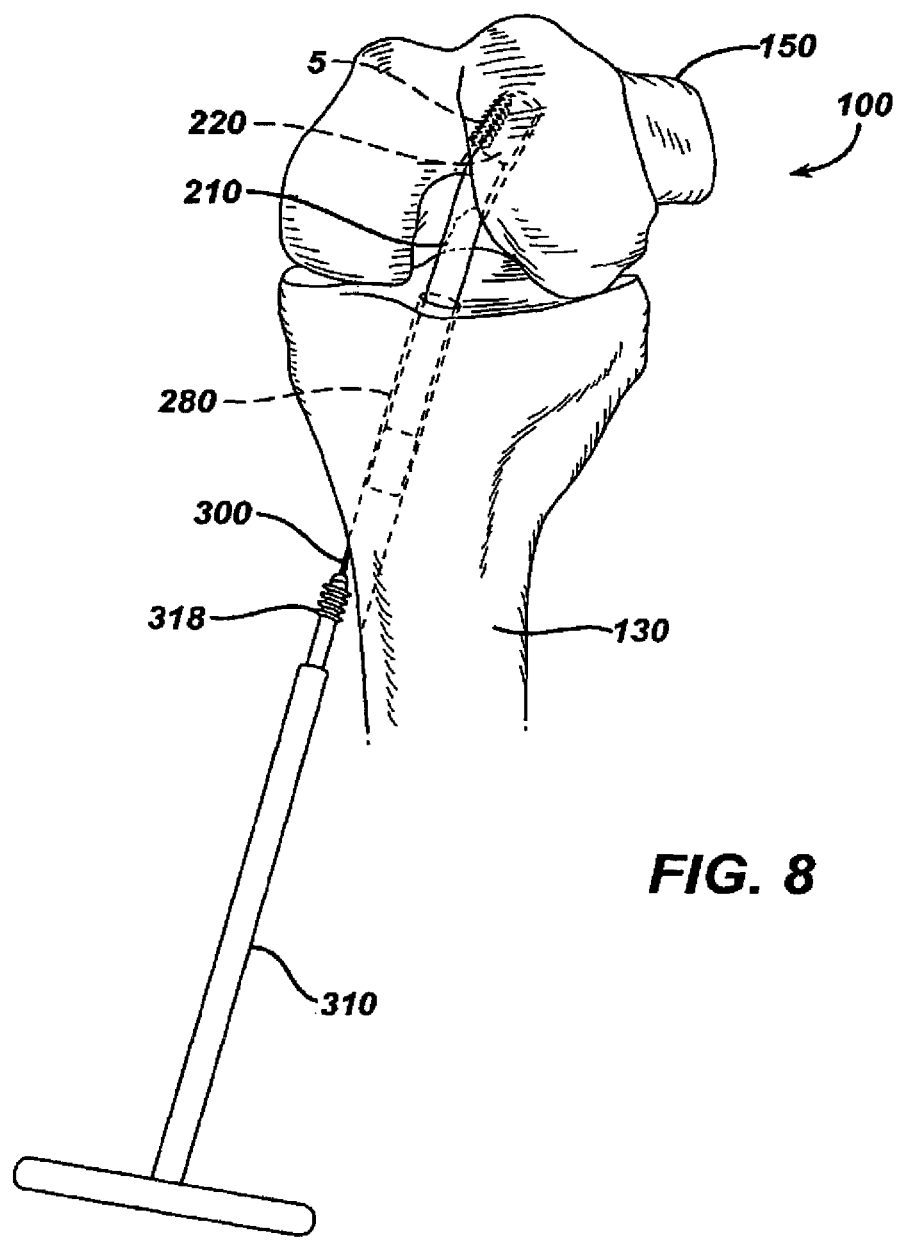
FIG. 8. illustrates a conventional tap device being used to tap a hole between the tunnel wall and the bone block.
Figure 9:
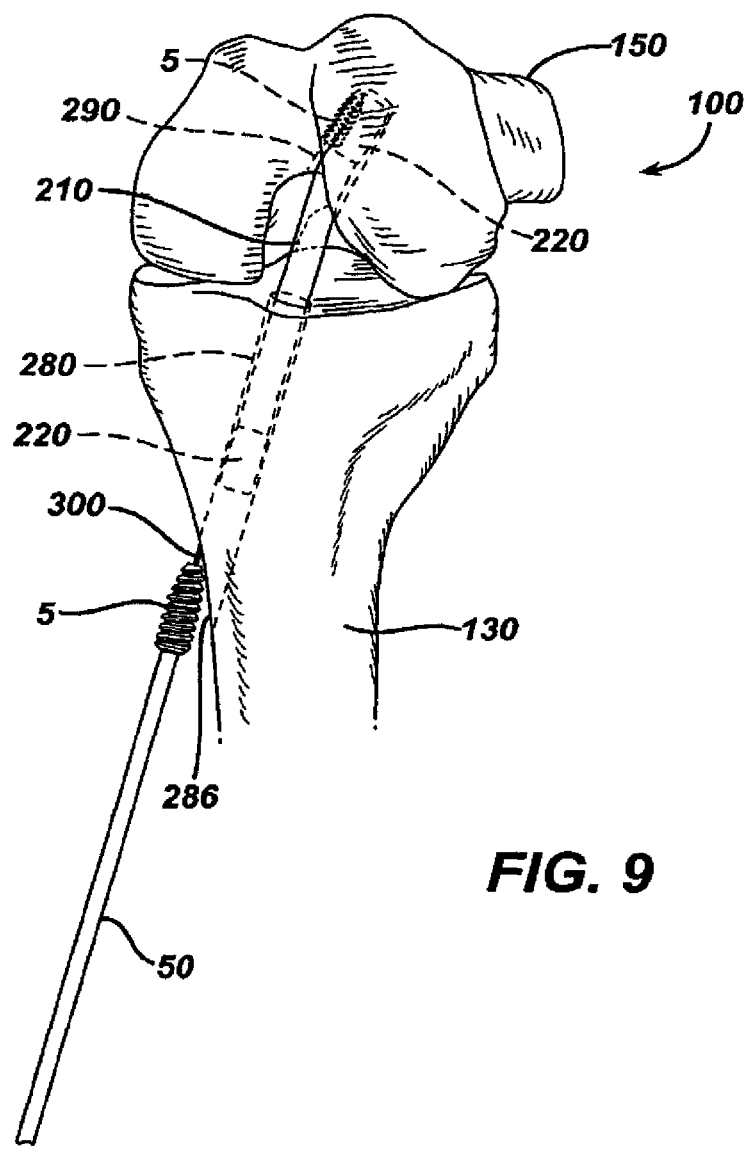
FIG. 9 illustrates the screw being inserted into the tibial tunnel between the tunnel wall and the bone block.
Figure 10:
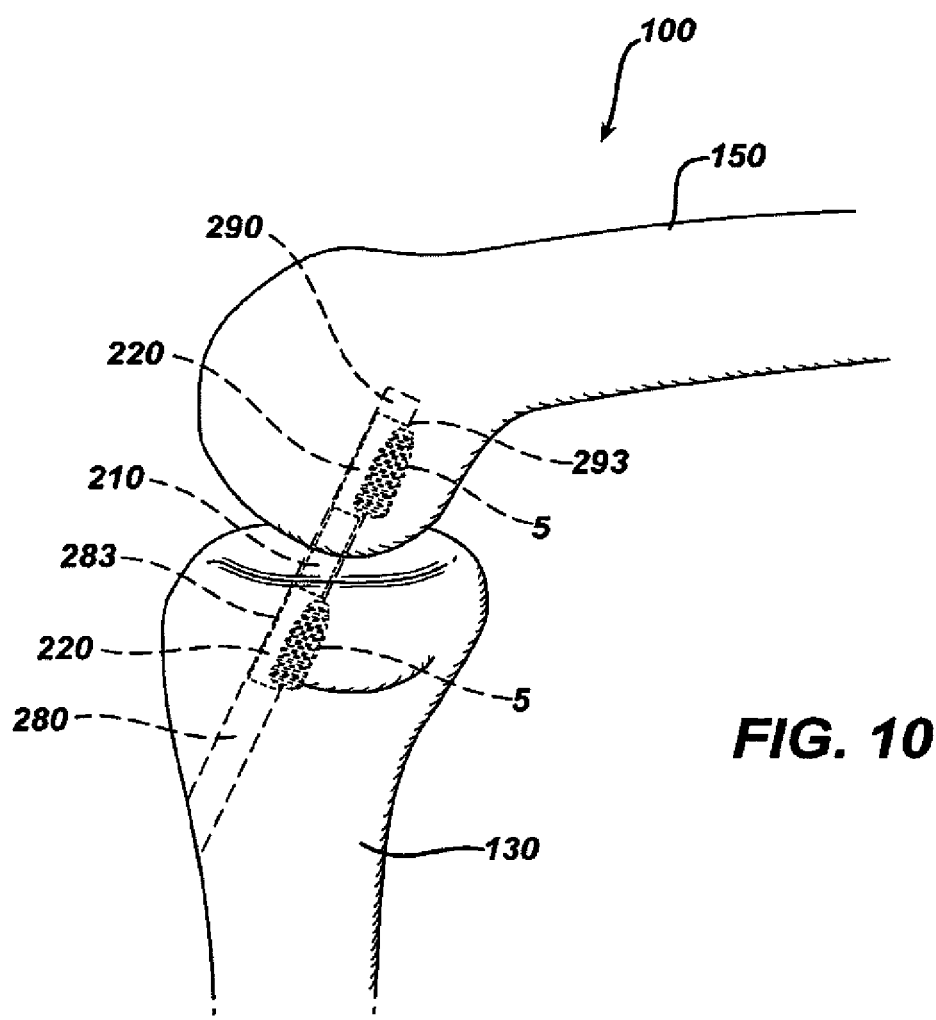
FIG. 10 is a side view of the knee after the ACL replacement procedure has been completed.

Referring to FIG. 3., the graft 200 is illustrated proximal to the knee 100 having the tibial tunnel 280 and femoral tunnel 290 drilled and reamed in the tibia 130 and femur 150, respectively. The guide pin 250 is seen to reside in the knee 100 with the elongated body 252 of guide pin 250 substantially contained within tibial tunnel 280 and femoral tunnel 290, with distal end 254 exiting out through opening 294 and proximal end 255 exiting out from opening 286. Next, the surgeon threads sutures 230 through the suture tunnels 222 in bone blocks 220. The suture through the top bone block 220 is also threaded through opening 257 of guide pin 250. The surgeon then pulls guide pin 250 distally such that the graft 200 is displaced into the knee 100 with upper bone graft 220 located in passage 292 of femoral tunnel 290 and lower bone block 220 located in passage 282 of tibial tunnel 280. An optional step of tapping the bone block and boned tunnel is illustrated in FIGS. 4 and 5. A guide wire 300 is seen to be inserted into femoral bone tunnel 290 between bone block 220 and inner tunnel wall 293. Then, a conventional cannulated bone tap 310 is inserted over guide wire 300. The bone tap 310 has elongated cannulated member 310, having a transverse handle 314 mounted to proximal end 312 and a tapping/cutting end 318 mounted to distal end 316. The tapping cutting end 318 is rotated by rotating handle 314, causing an opening to be cut and threads to be tapped between inner wall 293 and bone block 220 in the femoral tunnel 290. Then, as seen in FIG. 6, a biodegradable interference screw 5 mounted to a driver 50 is mounted to the guide wire 300 and threaded into the femoral tunnel 290 between the bone block 220 and the inner wall 293, thereby securing the upper bone block 220 in the passage 292 of femoral tunnel 290. The guide wire is then removed from the femoral tunnel 290 and inserted into opening 286 of and into passage 280 of tibial tunnel 280 between the lower bone block 220 and the inner wall 183 as seen in FIG. 7. Then, the surgeon tensions the graft 200 by pulling proximally on sutures 230 connected to lower bone block 220. Then, the bone tap 310 is inserted into tibial tunnel 280 over the guide wire 300 and an opening and threads are cut and tapped between inner wall 283, and bone block 220. Finally, the bone tap 310 is removed and as seen in FIG. 9, a biodegradable interference screw 5 is mounted over the guide wire 300 and threaded into the tibial tunnel 280 between inner wall 282 and lower bone block 220, thereby securing the lower bone block 220 in tibial tunnel 280. This completes the ACL reconstruction, and the graft 200 is now secured in the knee 100. The complete reconstructed knee 100 is seen in FIG. 10. The surgeon then checks the knee for proper flexion and completes the procedure in a conventional manner by removing the scope and portal, and conventionally closing and/or suturing and bandaging all incisions.

The following examples are illustrative of the principles and practice of the present invention although not limited thereto.

EXAMPLE 1

Figure 11A:
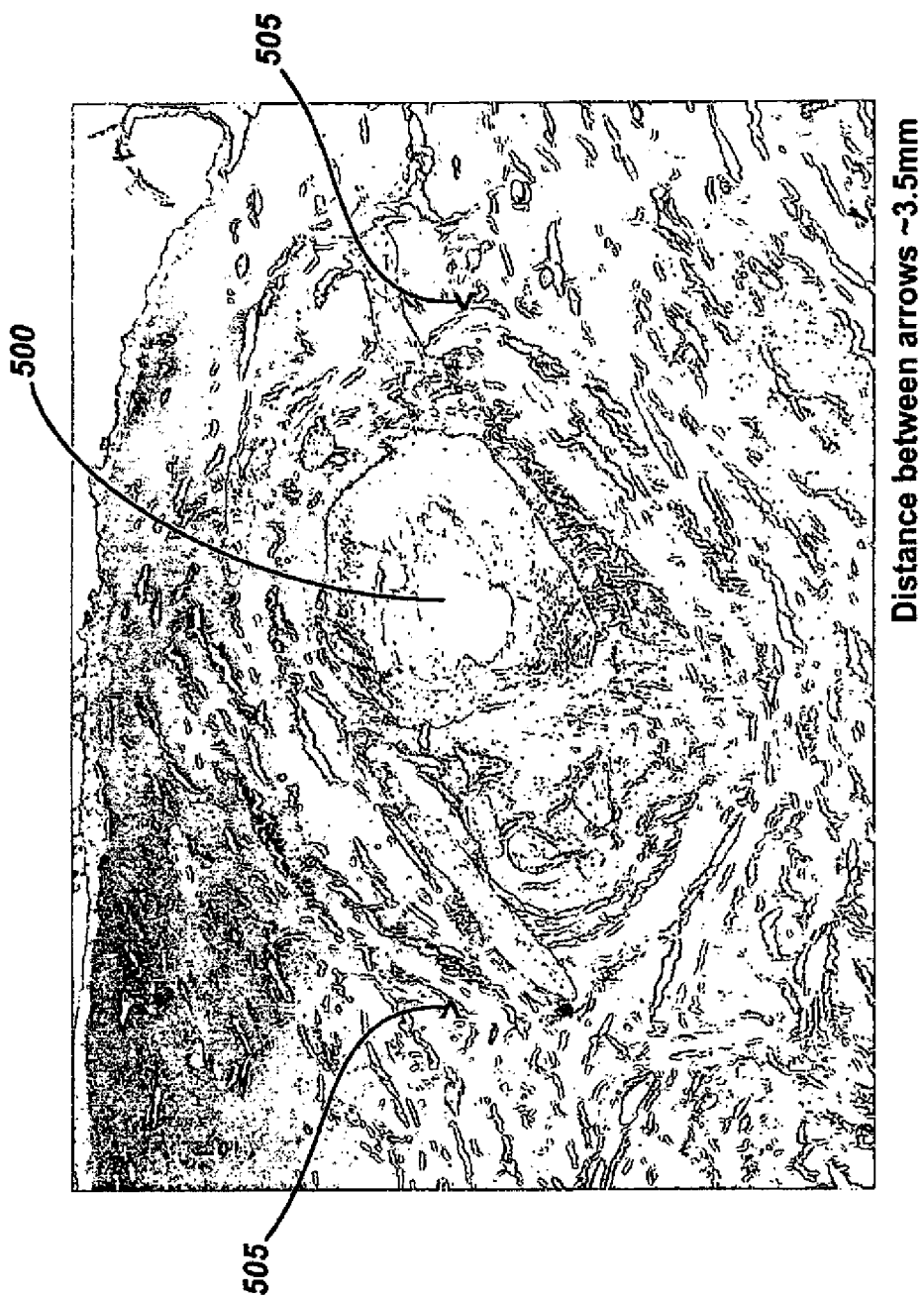
FIG. 11A is a histological section of a PLA/PGA bone pin containing [beta]-tricalcium phosphate and surrounding tissue.
Figure 11B:
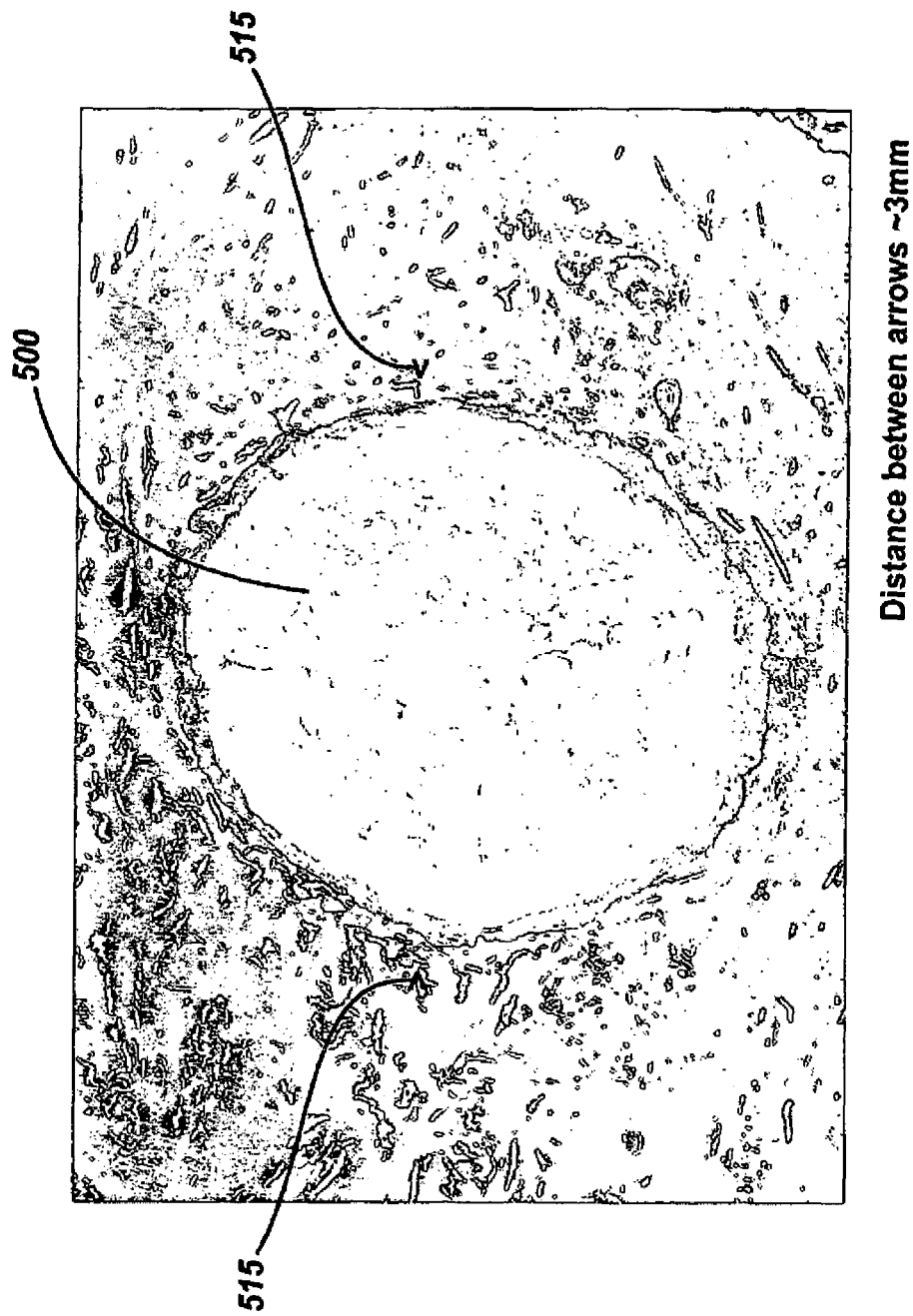
FIG. 11B is a histological section of a PLA bone pin and surrounding tissue.
Figure 11C:
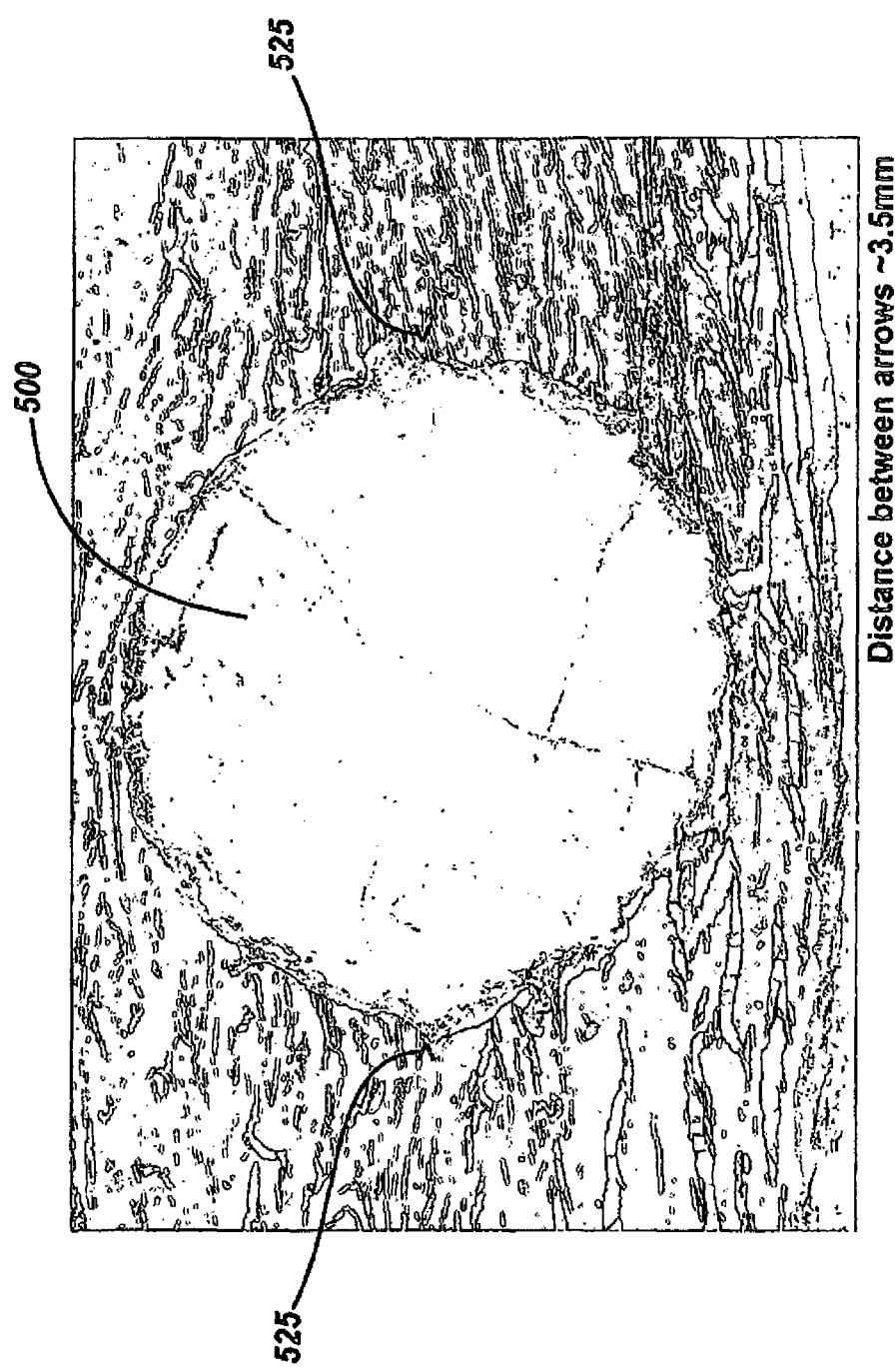
FIG. 11C is a histological section of a PLA bone pin and surrounding tissue.
Figure 11E:
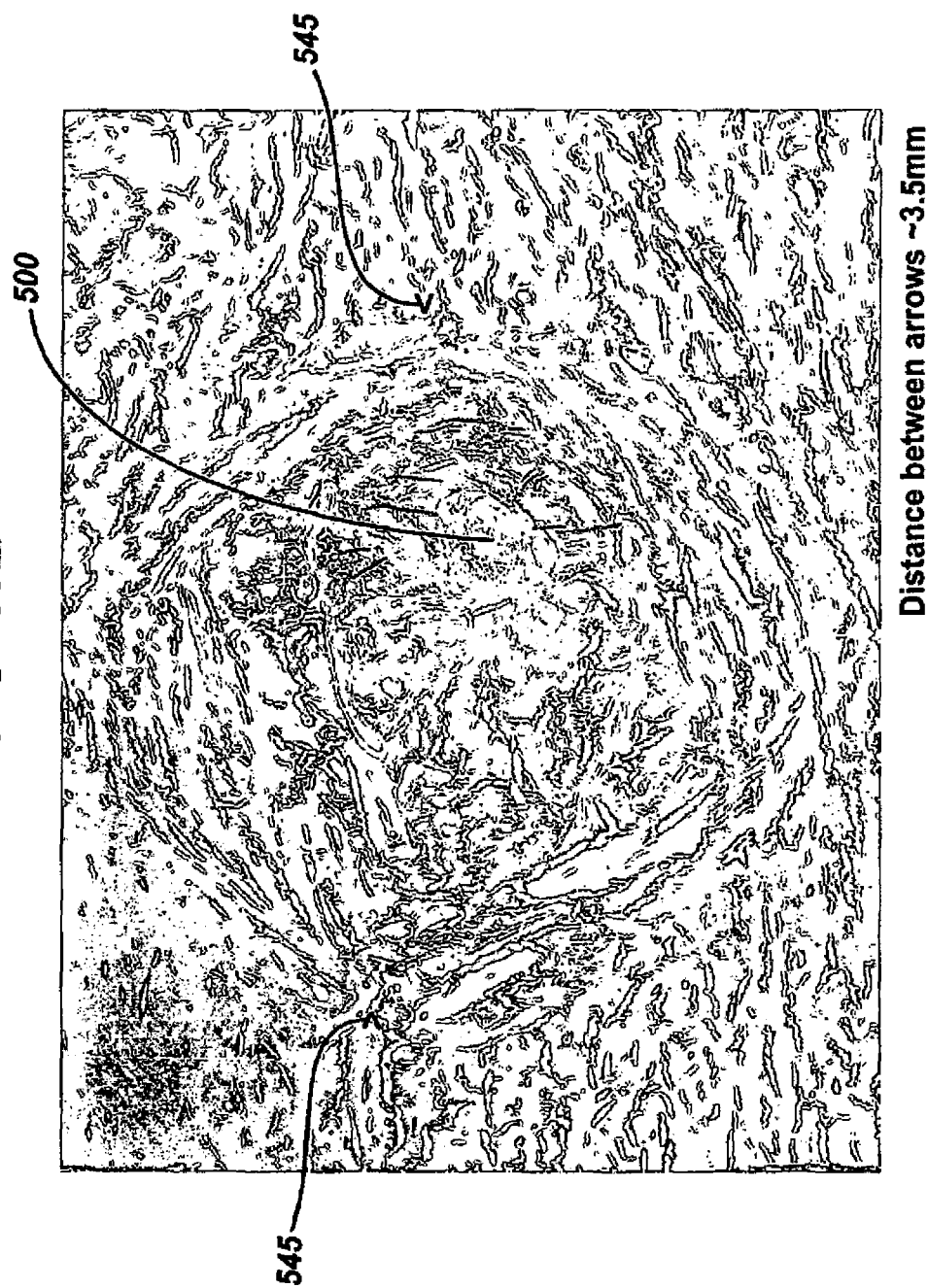
FIG. 11E is a histological section of a PLA/PGA bone pin containing [beta]-tricalcium phosphate and surrounding tissue.

Biodegradable composite bone pins 1 were prepared in a conventional manner and into the femurs of mammalian laboratory animals. The pins were of the following three compositions: A) composites of 15/85% by volume [beta]-tricalcium phosphate and (85/15) poly (lactide co-glycolide); B) poly(lactide); and C) composite of 15%/85% by volume [beta]-tricalcium phosphate and poly(lactide). About 24 months after implantation, the animals were euthanized and histological sections were obtained. As seen in FIG. 11A, a bone pin 500 having a Composition (A) demonstrated a significant degree of absorption when compared with the original diameter indicated by arrows 505, and significant tissue (bone) in-growth. In addition, minimal tissue reaction was observed. As seen if FIGS. 11B and 11C, bone pins 510 and 520 having Composition (B) exhibited minimal absorption compared with the original diameters indicated by arrows 515 and 525, respectively. As seen in FIG. 11D, a bone pin 530 having Composition C showed minimal absorption compared with the original diameter indicated by arrows 535. And, as seen in FIG. 11E, a bone pin 540 having Composition A demonstrated a significant degree of absorption compared with the original diameter indicated by arrows 545, and significant tissue (bone) in-growth. Minimal tissue reaction was observed.

The novel ACL graft replacement method of the present invention using a composite interference screw made from a bioaborbable polymer and a bioceramic or bioglass has many advantages. The advantages include having improved bioabsorption and bone replacement, improved tissue in-growth, and minimizing tissue trauma. In addition, there is an optimal balance between stiffness and elasticity of the screws.

Although this invention has been shown and described with respect to detailed embodiments thereof, it will be understood by those skilled in the art that various changes in form and detail thereof may be made without departing from the spirit and scope of the claimed invention.

What is claimed is:

1. A method of replacing an anterior cruciate ligament in a knee, comprising:
inserting a biodegradable composite interference screw into a bone tunnel between an interior surface of the bone tunnel and a first end of a graft mounted within the bone tunnel, said interference screw comprising a biodegradable comprising a copolymer of poly (lactic acid) and poly(glycolic acid), and a bioceramic; and
rotating the interference screw such that the screw is substantially contained within the bone tunnel, and the first end of the graft is fixed in place between the interference screw and a section of the interior surface of the bone tunnel;
wherein the biodegradable, composite interference screw degrades in the body.

2. The method of claim 1, further comprising inserting a second end of the graft into a second bone tunnel and anchoring the second end of the graft within the second bone tunnel.

3. The method of claim 1, wherein the bioceramic comprises a bioceramic selected from the group consisting of mono-, di-, tri, [alpha]-tri-, [beta]-tri and tetra-calcium phosphate, hydroxyapatite, calcium sulfates, calcium oxides, calcium carbonate, and magnesium calcium phosphates.

4. The method of claim 1, wherein the bioceramic comprises [beta]-tricalcium phosphate.

5. The method of claim 1, wherein the bioabsorbable polymer comprises a copolymer of polylactic acid and poly (glycolic acid) comprising about 85 mole percent to about 95 mole percent of poly (lactic acid) and about 5 mole percent to about 15 mole percent of poly (glycolic acid).

6. The method of claim 1, wherein the bioabsorbable polymer comprises a co-polymer of about 85 mole percent poly (lactic acid) and about 15 mole percent poly (glycolic acid).

7. The method of claim 1, wherein the composite screw comprises about 2.0 Volume percent to about 25.0 Volume percent of bioceramic.

8. The method of claim 1, wherein the composite screw comprises about 15.0 Volume percent of bioceramic.

9. The method of claim 1, wherein the graft has a bone block attached thereto.

10. The method of claim 1, further comprising tapping the inner surface of the bone tunnel to create a threaded space therein.

11. A biodegradable composite interference screw, comprising:

an elongate body having a cannulated passage extending therethrough between proximal and distal ends thereof such that the elongate body has a proximal opening and a distal opening, the elongate body having a thread formed on an outer surface thereof and extending between the proximal and distal ends, and the elongate body comprising a biodegradable polymer, and the biodegradable polymer comprising a copolymer of poly (lactic acid) and poly(glycolic acid), and a bioceramic, wherein the elongate body is configured to degrade when implanted in bone.

* * * * *